United States Patent
Dahl et al.

(10) Patent No.: US 7,027,862 B2
(45) Date of Patent: Apr. 11, 2006

(54) APPARATUS AND METHOD FOR TRANSMITTING AN ELECTRICAL SIGNAL IN AN IMPLANTABLE MEDICAL DEVICE

(75) Inventors: Roger Dahl, Andover, MN (US); Frank Dropps, Maple Grove, MN (US); Randy Nelson, Pine Springs, MN (US); Mark Stockburger, Inver Grove Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 542 days.

(21) Appl. No.: 10/202,920

(22) Filed: Jul. 25, 2002

(65) Prior Publication Data

US 2004/0019367 A1 Jan. 29, 2004

(51) Int. Cl.
*A61N 1/36* (2006.01)
*A61N 1/39* (2006.01)

(52) U.S. Cl. .................... 607/4; 607/5; 607/9
(58) Field of Classification Search .............. 607/2, 607/4–5, 9, 36–37, 66
See application file for complete search history.

(56) References Cited

U.S. PATENT DOCUMENTS

| | | | |
|---|---|---|---|
| 4,316,472 A | 2/1982 | Mirowski et al. | 607/9 |
| 4,375,817 A | 3/1983 | Engle et al. | 607/4 |
| 4,384,585 A | 5/1983 | Zipes | 607/5 |
| 4,577,633 A | 3/1986 | Berkovits et al. | 607/15 |
| 4,587,970 A | 5/1986 | Holley et al. | 607/15 |
| 4,726,380 A | 2/1988 | Vollmann et al. | 607/15 |
| 4,727,380 A | 2/1988 | Miura et al. | 347/238 |
| 4,727,877 A | 3/1988 | Kallok | 607/5 |
| 4,800,883 A | 1/1989 | Winstrom | 607/7 |
| 4,830,006 A | 5/1989 | Haluska et al. | 607/4 |
| 4,880,005 A | 11/1989 | Pless et al. | 607/15 |
| 4,949,719 A | 8/1990 | Pless et al. | 607/7 |
| 4,953,551 A | 9/1990 | Mehra et al. | 607/5 |
| 5,003,975 A | 4/1991 | Hafelfinger et al. | 607/28 |
| 5,117,824 A | 6/1992 | Keimel et al. | 607/4 |
| 5,163,427 A | 11/1992 | Keimel | 607/5 |
| 5,188,105 A | 2/1993 | Keimel | 607/5 |
| 5,331,966 A | 7/1994 | Bennett et al. | 600/508 |
| 5,713,926 A * | 2/1998 | Hauser et al. | 607/5 |
| 6,280,462 B1 | 8/2001 | Hauser et al. | 607/5 |
| 6,704,598 B1 * | 3/2004 | Ding et al. | 607/9 |
| 6,735,472 B1 * | 5/2004 | Helland | 607/5 |

(Continued)

FOREIGN PATENT DOCUMENTS

EP 0 627 237 7/1994

(Continued)

*Primary Examiner*—Carl Layno
(74) *Attorney, Agent, or Firm*—Paul H. McDowall; Girma Wolde-Michael; Michael C. Soldner (57) ABSTRACT

A method and device for transmitting a signal in an implantable medical device that includes a control unit and a first electrode and a second electrode positioned along a lead body. A connector block is positioned along an upper portion of a housing portion of the control unit, and a connector is positioned at a proximal portion of the lead body and is insertable within the connector block. A third electrode having a conductive element is positioned along the control unit in close proximity adjacent to the connector. The control unit transmits a signal between the first electrode and the second electrode and determines an alternate transmission path of the signal between the third electrode and one or both of the first electrode and the second electrode in response to the signal not being effectively transmitted between the first electrode and the second electrode.

20 Claims, 8 Drawing Sheets

U.S. PATENT DOCUMENTS

| | | | |
|---|---|---|---|
| 6,751,502 B1 * | 6/2004 | Daum et al. | 607/8 |
| 6,804,555 B1 * | 10/2004 | Warkentin | 607/9 |
| 2002/0072773 A1 | 6/2002 | Bardy et al. | |
| 2002/0151935 A1 * | 10/2002 | Levine | 607/9 |
| 2003/0120313 A1 * | 6/2003 | Begemann et al. | 607/9 |

FOREIGN PATENT DOCUMENTS

| | | |
|---|---|---|
| WO | WO92/18198 | 10/1992 |
| WO | WO02/34332 | 5/2002 |
| WO | WO 02/068043 A1 * | 9/2002 |

* cited by examiner

APPARATUS AND METHOD FOR TRANSMITTING AN ELECTRICAL SIGNAL IN AN IMPLANTABLE MEDICAL DEVICE

BACKGROUND OF THE INVENTION

1. Field of the Invention

The present invention relates to a method and apparatus for transmitting an electrical pulse in body tissue, and in particular, the present invention relates to a method and apparatus for transmitting an electrical signal between an electrode positioned on a housing of an implantable medical device and electrodes positioned along a lead body of the device.

2. Description of the Related Art

Since the introduction of the first implantable pacemakers in the 1960s, there have been considerable advancements in both the fields of electronics and medicine, leading to a wide assortment of commercially available implantable medical devices. These implantable medical devices include therapeutic and diagnostic devices, such as pacemakers, cardioverters, defibrillators, neural stimulators, and drug administering devices, among others. Today's state-of-the-art implantable medical devices are vastly more sophisticated and complex than their early counterparts, and are capable of performing significantly more complex tasks and providing increased therapeutic benefits.

Such implantable medical devices generally include a control unit, implanted within the patient's body, that is capable of delivering electrical signals to or receiving electrical signals from one or more leads extending from the control unit to an area of the body being treated, for example, the heart, a nerve bundle, or the like. The control unit is generally housed within a biologically inert, electrically conductive can. In certain cases, the can may be used as an electrode itself. For example, electrical signals (e.g., pacing signals, neural stimulation signals, defibrillating pulses, and the like) emitted from one or more lead electrodes may be received by the can after traveling through the body. Depending upon the type and magnitude of the signal, muscle tissue in close proximity to the electrically conductive can may be stimulated as a result of the electrical interface effects between the can and the surrounding muscle tissue.

Further, it may be desirable in certain cases to transmit a pacing, stimulation, or defibrillation signal or signals through tissue between two electrodes disposed along the lead. However, in certain situations it may not be possible to ensure with absolute certainty that both electrodes will be in adequate electrical contact with the tissue. Thus, in such situations the signal or signals may not be successful in affecting the tissue as desired.

SUMMARY OF THE INVENTION

The present invention is directed to an implantable medical device having an elongated lead body that extends from a proximal portion to a distal portion, a first electrode and a second electrode positioned along the lead body, a housing having an upper portion, and a control unit. A housing portion of the control unit houses electrical components of the implantable medical device, and a connector block is positioned along an upper portion of the housing portion. A connector is positioned at the proximal portion of the lead body and is insertable within the connector block to electrically couple the plurality of electrodes and the electrical components. A third electrode having a conductive element is positioned along the control unit in close proximity adjacent to the connector. The control unit transmits a signal between the first electrode and the second electrode and determines an alternate transmission path of the signal between the third electrode and one or both of the first electrode and the second electrode in response to the signal not being effectively transmitted between the first electrode and the second electrode.

According to one aspect of the present invention, the determination of the alternate transmission path corresponds to determining which of the first electrode and the second electrode are in sufficient contact with the patient's heart.

According to yet another aspect of the present invention, the alternate transmission path is determined to be between the third electrode and one of the first electrode, the second electrode and both the first electrode and the second electrode in response to determining the therapy is not successful.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Figure 1:
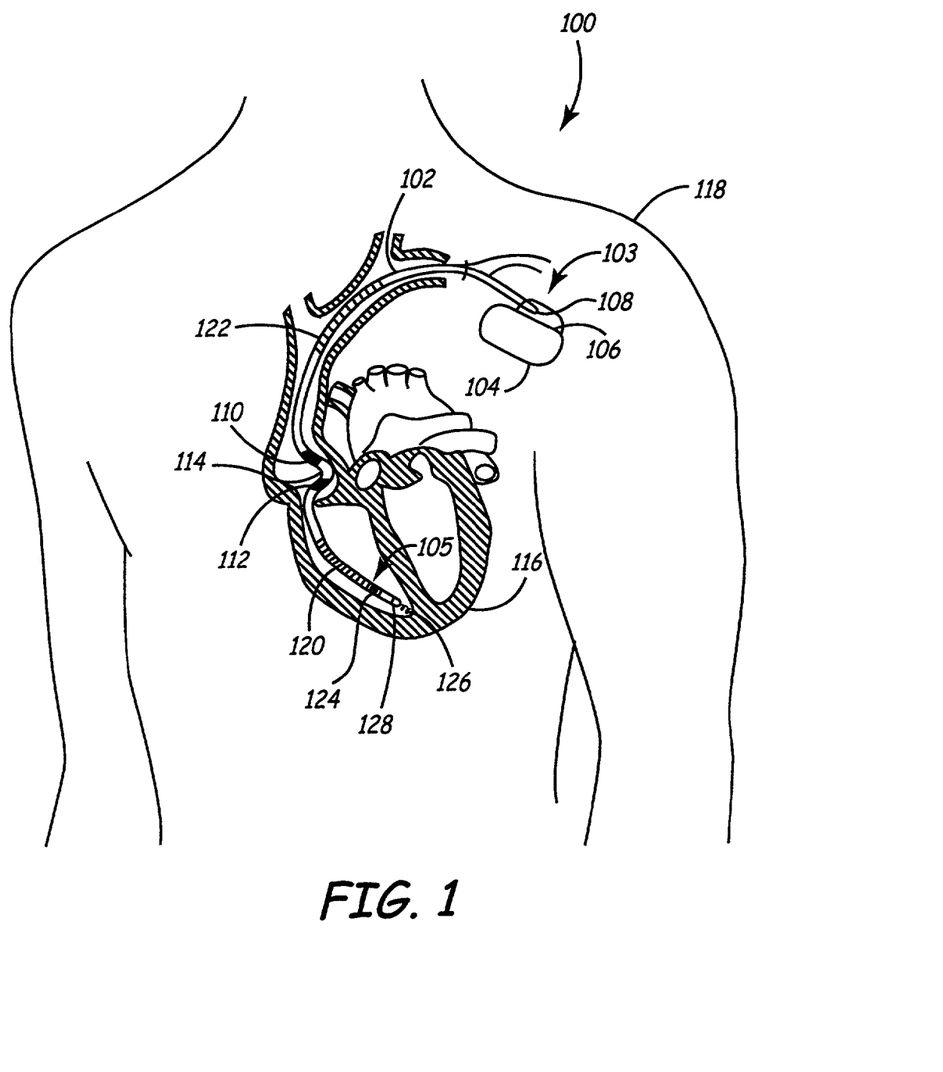
FIG. 1 is a schematic diagram of an implantable medical device for transmitting an electrical pulse according to the present invention.

FIG. 1 is a schematic diagram of an implantable medical device for transmitting an electrical pulse according to the present invention. As illustrated in FIG. 1, an implantable medical device 100 of the present invention includes an elongated insulated lead body 102 extending from a proximal portion 103 to a distal portion 105 and insertable within a control unit 104. Control unit 104 includes a biologically inert conductive housing 106 housing electronic components (FIG. 2) and a power source (not shown), and a biologically inert connector block 108 through which an electrical interconnection or interconnections are made between lead body 102 and the electronic components housed within conductive housing 106.

A first lead electrode 110 and a second lead electrode 112, such as ring electrodes, for example, are located along a curved portion 114 of lead body 102 and electrically coupled to control unit 104. Lead body 102 is positioned within a heart 116 of a patient 118 so that electrode 110 and electrode 112 located within the atrium of heart 116 so as to be employed for atrial pacing and for sensing atrial depolarizations.

Elongated coil electrodes 120 and 122 are position along lead body 102, and are employed in conjunction with conductive housing 106 for delivery of defibrillation pulses. In addition, a ring electrode 124 and an extendable helix 126 mounted retractably within an insulated electrode head 128 are located along distal portion 105 of lead body 102 and are employed for cardiac pacing and for sensing ventricular depolarizations. Finally, a connector pin 130 (shown in FIG. 3) located at proximal portion 103 of lead body 102 is insertable within connector block 108 to electrically couple control unit 104 to electrodes 110, 112 and 120–126.

Although lead electrodes 110, 112 and 124 are shown in FIG. 1 as being ring electrodes, it is understood that the present invention is not intended to be limited to the use of ring electrodes, but rather encompasses other specific types of electrodes.

Figure 2:
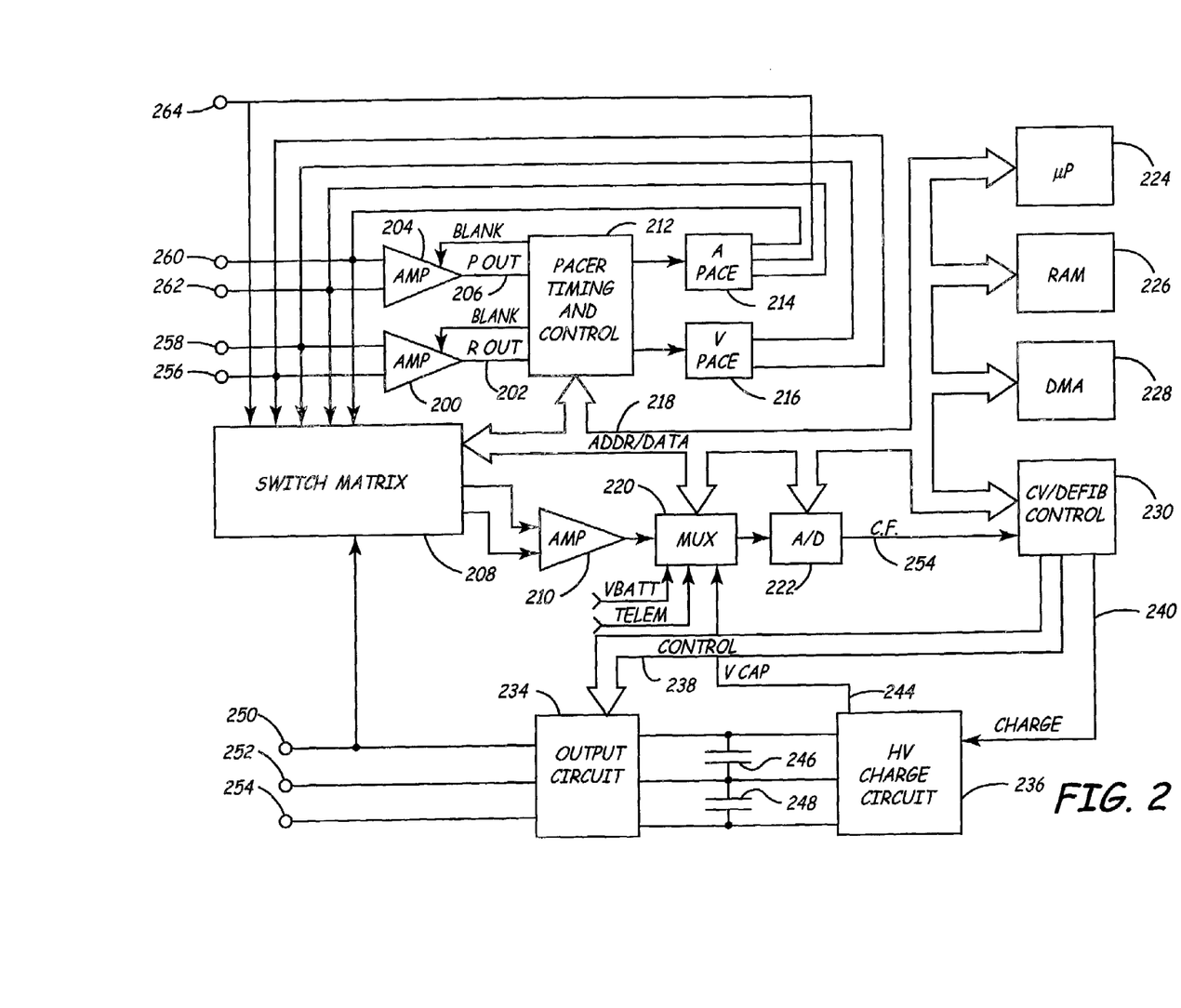
FIG. 2 is a functional schematic diagram of an implantable medical device according to the present invention.

FIG. 2 is a functional schematic diagram of an implantable medical device according to the present invention. It is understood that FIG. 2 should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices that deliver different forms of anti-arrhythmia therapies, nerve stimulation or drug administration.

As illustrated in FIG. 1, implantable medical device 100 is provided with a lead system including electrodes, which may be as illustrated in FIG. 1. However, it is understood that alternate lead systems may of course be substituted. If the electrode configuration of FIG. 1 is employed, the correspondence to the illustrated electrodes in FIG. 2 is as follows. Electrode 250 corresponds to conductive housing 106, and is the uninsulated portion of the housing of the implantable medical device. Electrode 252 corresponds to electrode 120 and is a defibrillation electrode located in the right ventricle. Electrode 254 corresponds to electrode 122 and is a defibrillation electrode located in the superior vena cava. Electrodes 256 and 258 correspond to electrodes 124 and 126, and are used for sensing and pacing in the ventricle. Electrodes 260 and 262 correspond to electrodes 110 and 112 and are used for pacing and sensing in the atrium. Finally, electrode 264 corresponds to electrode 107 (FIG. 3) and is used for transmitting an electrical pulse according to the present invention, as described below.

In alternate embodiments described in detail below, electrode 250 corresponds to conductive housing 406 (FIG. 6), and is the uninsulated portion of the housing of the implantable medical device. Electrode 252 corresponds to electrode 420 and is a defibrillation electrode located in the right ventricle. Electrode 254 corresponds to electrode 422 and is a defibrillation electrode located in the superior vena cava. Electrodes 256 and 258 correspond to electrodes 424 and 426, and are used for sensing and pacing in the ventricle. Electrodes 260 and 262 correspond to electrodes 410 and 412 and are used for pacing and sensing in the atrium. Finally, electrode 264 corresponds to electrode 407 (FIG. 6) and is used for transmitting an electrical pulse according to the present invention, as described below.

As illustrated in FIG. 2, electrodes 250–254 are coupled to high voltage output circuit 234. Electrodes 256 and 258 are located on or in the ventricle and are coupled to an R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 256 and 258 exceeds the present sensing threshold.

Electrodes 260 and 262 are located on or in the atrium and are coupled to a P-wave amplifier 204, which preferably also takes the form of an automatic gain controlled amplifier providing an adjustable sensing threshold as a function of the measured R-wave amplitude. A signal is generated on Pout line 206 whenever the signal sensed between electrodes 260 and 262 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Electrode 264 is located along housing 106, 406 of control unit 104, 404 for delivering therapy according to the present invention, as described in detail below.

Switch matrix 208 is used to select which of the available electrodes are coupled to wide band (0.5–200 Hz) amplifier 210 for use in digital signal analysis. Selection of electrodes 250–264 is controlled by microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 256–262. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used in conjunction with the present invention to diagnose the occurrence of a variety of tachyarrhythmias.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of re-circulating buffers, capable of holding series of measured intervals, which may be analyzed in response to the occurrence of a pace or sense interrupt to determine whether the patient's heart is presently exhibiting atrial or ventricular tachyarrhythmia.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Hess et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Patent Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 106, 406 (FIGS. 3, 4, 6 and 7) serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry that may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, the typical therapy will be delivery of a high amplitude defibrillation pulse, typically in excess of 5 joules. Lower energy levels may be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such preset therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 3:
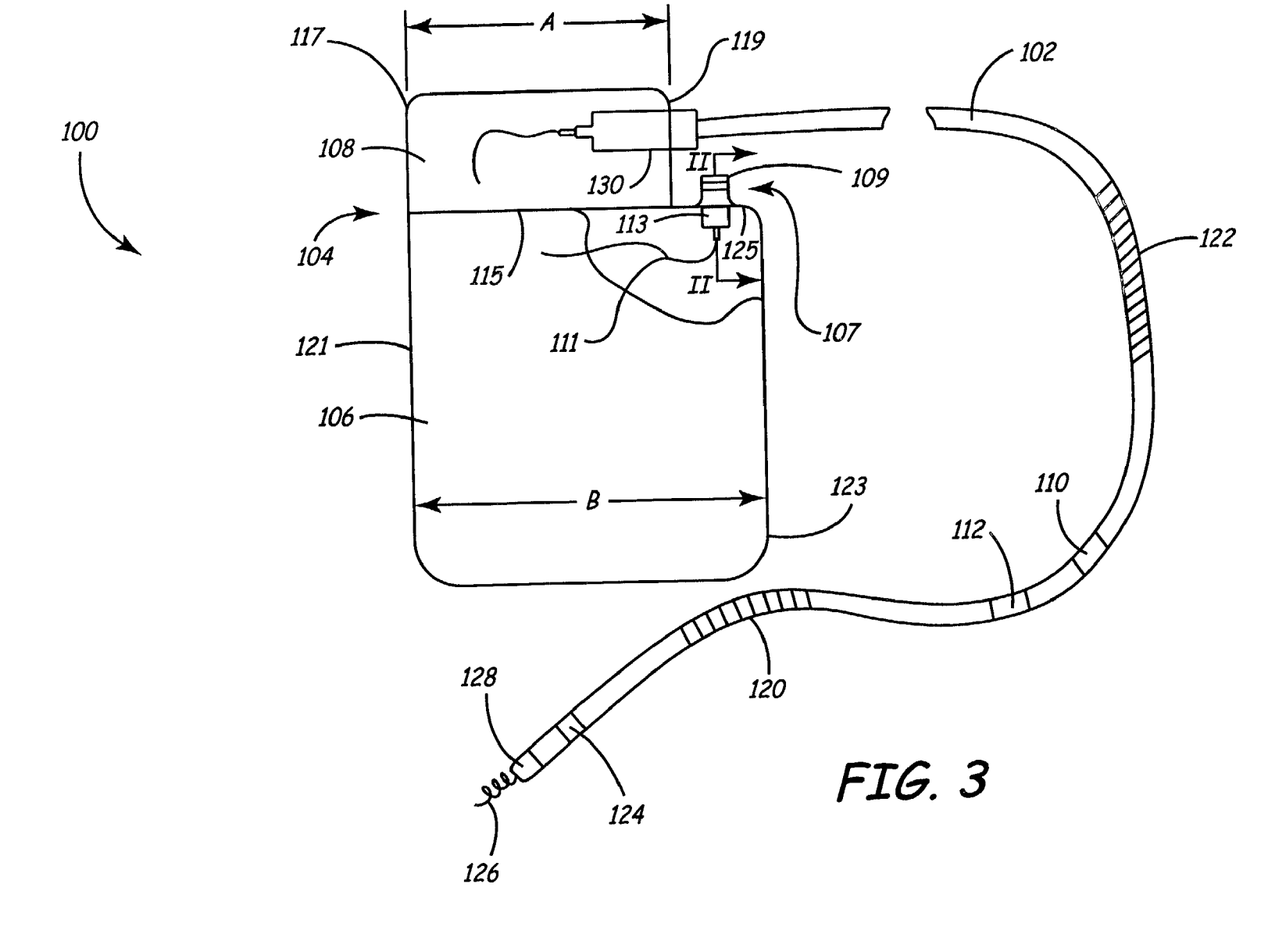
FIG. 3 is a schematic diagram of an implantable medical device for transmitting an electrical pulse according to the present invention.

FIG. 3 is a schematic diagram of an implantable medical device for transmitting an electrical pulse according to the present invention. As illustrated in FIG. 3, implantable medical device 100 further includes an electrode 107 having an integral conductive element 109 and a feedthrough 113. A conductor 111 extends from electrode 107 to one or more electrical components housed within conductive housing 106. According to a preferred embodiment of the present invention, electrode 107 is preferably a glass or ceramic material.

As illustrated in FIG. 3, connector block 108 is positioned along an upper portion 115 of housing 106, with connector block 108 extending a length A from a back portion 117 to a front portion 119 and housing 106 extending a length B from a back portion 121 to a front portion 123. Length A of connector block 108 is less than length B of housing 106, so that a portion 125 of upper portion 115 of housing 106 extends outward from front portion 119 of connector block 108. As a result, connector 130 of lead 102 is positioned over outward extending portion 125 of upper portion 115 of housing 106 when inserted within connector block 108. According to the present invention, electrode 107 is positioned along control unit 104 so as to be in close proximity to connector 130 of lead body 102. In particular, as illustrated in FIG. 3, electrode 107 is positioned along outward extending portion 125 of upper portion 115 of housing 106, adjacent to connector 130 when connector 130 is inserted within connector block 108. As a result, by positioning electrode 107 to be in close proximity adjacent to connector 130 when lead body 102 is engaged with connector block 108, the present invention reduces the likelihood of direct muscle contact with the conductive element 109 of electrode 107, reducing muscle stimulation around implantable medical device 100 during delivery of therapy by implantable medical device 100.

Figure 4:
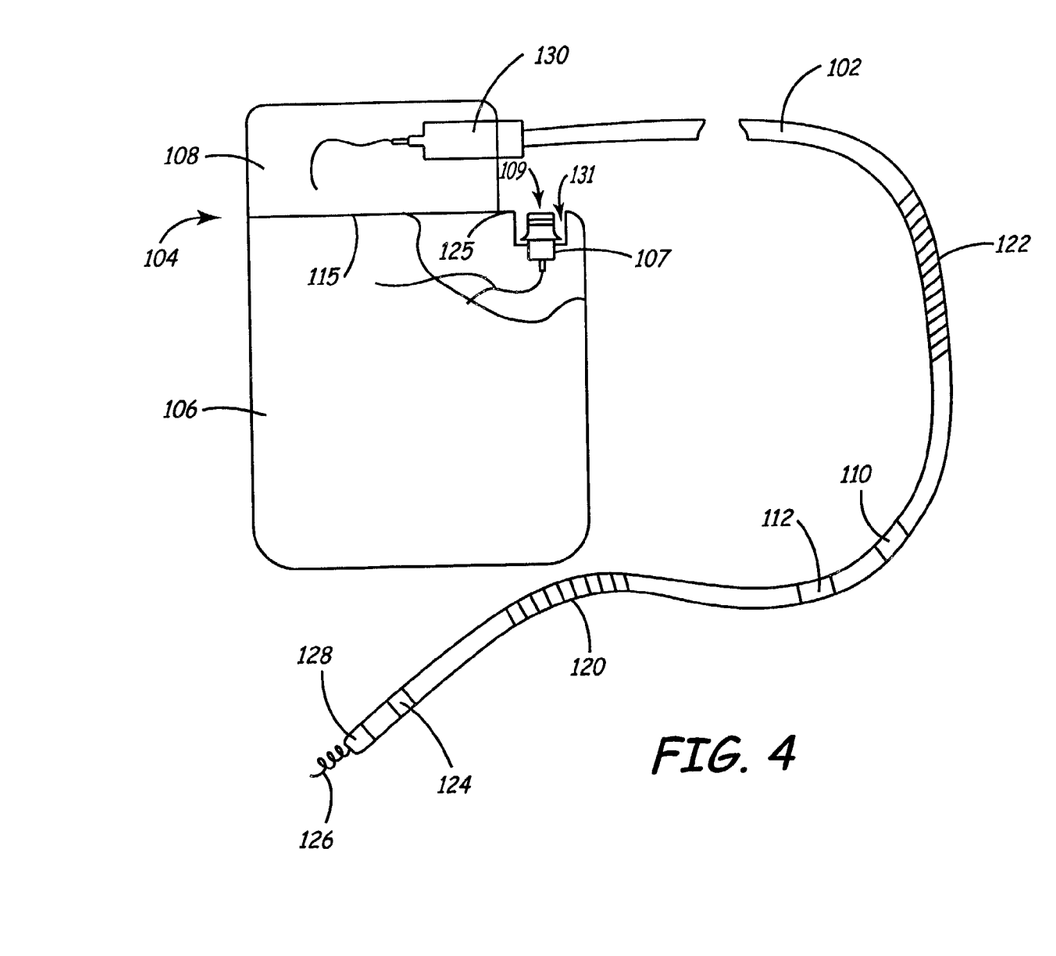
FIG. 4 is a schematic diagram of an implantable medical device for transmitting an electrical pulse according to an alternate embodiment of the present invention.

FIG. 4 is a schematic diagram of an implantable medical device for transmitting an electrical pulse according to an alternate embodiment of the present invention. As illustrated in FIG. 4, according to the alternate embodiment of the present invention, electrode 107 is positioned along housing 106 so as to be in close proximity to connector 130 of lead body 102. In particular, according to an alternate embodiment of the present invention, electrode 107 is positioned, similar to the embodiment of FIG. 3, to be located in close proximity adjacent to connector 130 along outward extending portion of upper portion 115 of housing 106 so that when lead body 102 is engaged with connector block 108, direct muscle contact with conductive element 109 of electrode 107 is less likely to occur.

However, in the alternate embodiment illustrated in FIG. 4, electrode 107 is also embedded within implantable medical device 100. In particular, for example, as illustrated in FIG. 4, electrode 107 is positioned within an opening 131 located along outward extending portion 125 of housing 106 so that conductive element 109 is positioned below upper portion 115 of housing 106. In this way, by positioning electrode 107 in close proximity adjacent to connector 130 and embedding electrode 107 within housing 106 of implantable medical device 100, the present invention further reduces the likelihood of direct muscle contact with the conductive element 109 of electrode 107, reducing muscle stimulation around implantable medical device 100 during delivery of therapy by implantable medical device 100.

Figure 5:
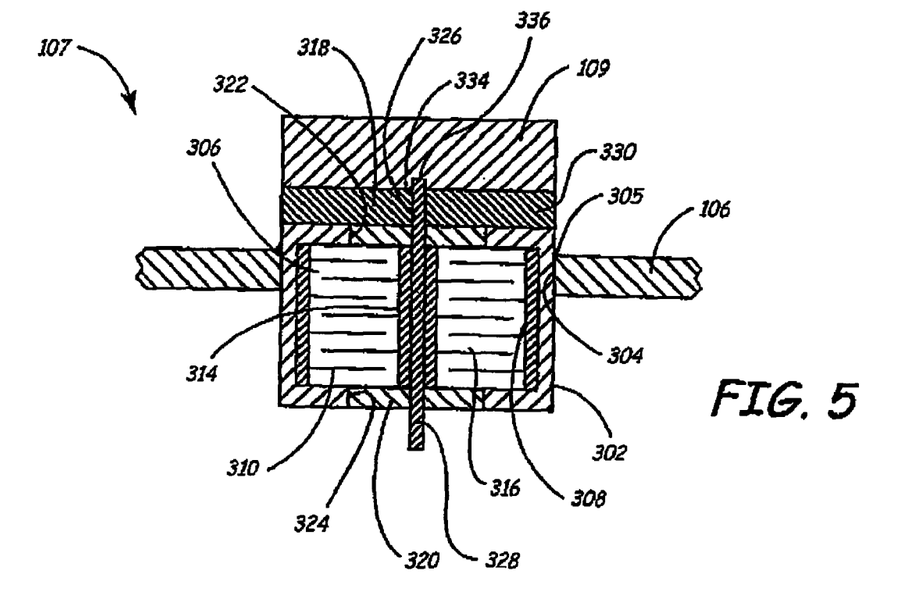
FIG. 5 is a cross-sectional view of an electrode according to the present invention, taken along cross-sectional line II—II of the implantable medical device of FIG. 3.

FIG. 5 is a cross-sectional view of an electrode according to the present invention, taken along cross-sectional line II—II of the implantable medical device of FIG. 3. As illustrated in FIG. 5, electrode 107 includes a hermetically sealed capsule 302 that, in the illustrated embodiment, extends within housing 106 through an opening 304 defined by housing 106. In the illustrated embodiment, capsule 302 is attached to housing 106 by a weld 305, sealing any space left between capsule 302 and opening 304 in housing 106. A capacitor 306 is disposed within capsule 302 and is adhesively attached within capsule 302 by an electrically conductive adhesive 308 such that a first set of plates 310 are electrically coupled with capsule 302. A pin 312 extends through capacitor 306 and is adhesively attached to capacitor 306 by an electrically conductive adhesive 314 such that a second set of plates 316 of capacitor 306 are electrically coupled with pin 312. Electrically conductive adhesive 308 and electrically conductive adhesive 314 may be made from the same or different adhesive materials.

Still referring to FIG. 5, capsule 302 further includes a first insulator 318 and a second insulator 320 disposed in and sealed to a first opening 322 and a second opening 324, respectively, defined by capsule 302. First insulator 318 and second insulator 320 define openings 326 and 328 therein, respectively, through which pin 312 extends. Thus, first insulator 322 and second insulator 324 provide electrical insulation between pin 312 and capsule 302. Electrode 107 further includes a dielectric spacer 330, attached to capsule 302, which defines an opening 334 through which pin 312 extends. Conductive element 109 is attached to dielectric spacer 330 such that dielectric spacer 330 provides electrical insulation between conductive element 109 and capsule 302. Conductive element 109 defines a bore 336 for receiving pin 312 and for providing an electrical connection between pin 312 and conductive element 109. Conductor 111 is attached to pin 312 to electrically couple pin 312 with one or more electrical components (not shown) housed within housing 106, as illustrated in FIG. 3.

In certain cases, it may be desirable to transmit signals (e.g., pacing signals, stimulation signals, defibrillation signals, or the like) between first lead electrode 110 and second lead electrode 112, i.e., in a bipolar fashion. However, in order for a signal to be effectively transferred between electrodes 110 and 112 to appropriately stimulate the patient's heart, it is important that electrodes 110 and 112 be in sufficient electrical contact with the tissue surrounding the area where electrodes 110 and 112 are placed within patient 118. According to the present invention, once a signal has transmitted between electrodes 110 and 112, microprocessor 224 determines whether electrodes 110 and 112 are in sufficient contact with tissue of patient 118 to appropriately stimulate heart 116. For example, microprocessor 224 determines whether the signal is effectively transmitted between electrodes 110 and 112 by examining the amplitude of subsequent p-waves sensed at electrodes 110 and 112 and determining that electrodes 110 and 112 are not in sufficient contact when the amplitude is less than a predetermined value. If electrodes 110 and 112 are determined not to be in sufficient contact, microprocessor 224 then switches transmission of the signal, through switch matrix 208, so that the signal is transmitted between electrode 107 and one or both of electrodes 110 and 112 based upon review of the corresponding evoked response. In this way, the present invention provides an alternate path for the signals, such that signals transmitted from the one of lead electrode 110 and lead electrode 112 that is in sufficient electrical contact with the tissue of the body is transmitted through the body to conductive element 109. As a result, a desired signal may be transmitted to the tissue of the body even though signals cannot be effectively transmitted between lead electrode 110 and lead electrode 112.

In addition, as described above, by positioning electrode 107 within close proximity to connector 130 of lead body 102, according to the present invention, muscle stimulation during delivery of therapy by implantable medical device is reduced when electrode 107 is utilized.

Figure 6:
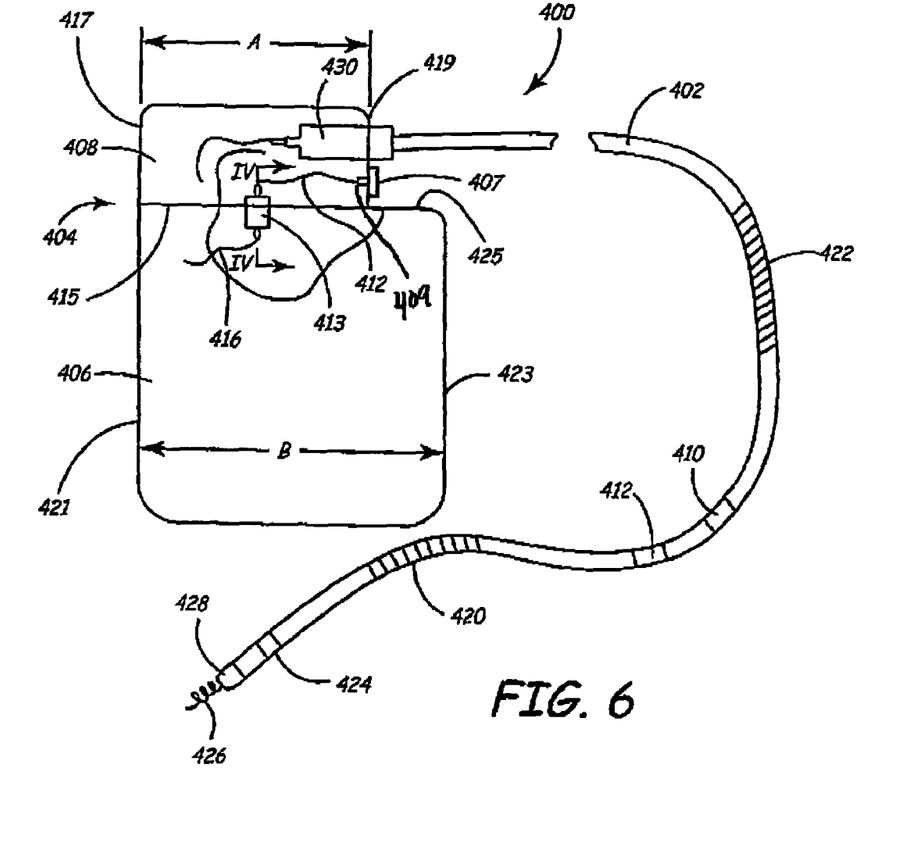
FIG. 6 is a schematic diagram of an implantable medical device for transmitting an electrical pulse according to an alternate embodiment of the present invention.

FIG. 6 is a schematic diagram of an implantable medical device for transmitting an electrical pulse according to an alternate embodiment of the present invention. As illustrated in FIG. 6, an implantable medical device 400 according to an alternate embodiment of the present invention, is similar to implantable medical device 100 described in reference to FIGS. 3–5, and includes an elongated insulated lead body 402 extendable from a control unit 404 that includes a biologically inert conductive housing 406 housing electronic components (not shown) and a power source (not shown), and a biologically inert connector block 408 through which an electrical interconnection or interconnections are made between lead body 402 and the electronic components housed within conductive housing 406. Implantable medical device 400 further includes an electrode 407 that includes a conductive element 409 coupled to a feedthrough 413 via a first conductor 412. Electrode 407 is electrically interconnected with one or more of the electronic components housed within housing 406 via the first conductor 412, the feedthrough 413, and a second conductor 416. According to a preferred embodiment of the present invention, electrode 407 is preferably a glass or ceramic material.

Although only a single feedthrough 413 is shown in FIG. 6, it is understood that device 400 of the present invention could include multiple feedthroughs leading to multiple connection points, and that a single feedthrough is illustrated merely for brevity.

A first lead electrode 410 and a second lead electrode 412, such as ring electrodes, for example, are located along lead body 402 and electrically coupled to control unit 404. First lead electrode 410 and second lead electrode 412 are employed for atrial pacing and for sensing atrial depolarizations.

Elongated coil electrodes 420 and 422 are positioned along lead body 402, and are employed in conjunction with conductive housing 406 for delivery of defibrillation pulses. In addition, a ring electrode 424 and an extendable helix 426, mounted retractably within an insulated electrode head 427, are employed for cardiac pacing and for sensing ventricular depolarizations. Finally, a connector pin 430 located at a proximal end of lead body 402 is removably insertable within connector block 408 to electrically couple control unit 404 to electrodes 410, 412 and 420–426.

Although lead electrodes 410, 412 and 424 are shown in FIG. 6 as being ring electrodes, it is understood that the present invention is not intended to be limited to the use of ring electrodes, but rather encompasses other specific types of electrodes. Normal functional operation of electrodes 410, 412 and 420–426 of implantable medical device 400 is similar to operation of electrodes 110, 112 and 120–126 of implantable medical device 100, and therefore the description of implantable medical device 400 with reference to FIG. 2 is omitted merely for the sake of brevity.

As illustrated in FIG. 6, connector block 408 is positioned along an upper portion 415 of housing 406, and extends a length A from a back portion 417 to a front portion 419, and housing 406 extends a length B from a back portion 421 to a front portion 423. Length A of connector block 408 is less than length B of housing 406, so that an outward extending portion 425 of upper portion 415 of housing extends outward from front portion 419 of connector block 408. As a result, connector 430 of lead 402 is positioned over outward extending portion 425 of upper portion 415 of housing 406 when connector 430 is inserted within connector block 408, similar to implantable medical device 100 described above in reference to FIG. 3. According to the present invention, electrode 407 of the alternate embodiment is positioned along control unit 404 so that conductive element 409 is in close proximity to connector 430 of lead body 402. In particular, as illustrated in FIG. 6, conductive element 409 of electrode 407 is positioned along front portion 419 of connector block 408, adjacent to connector 430 when connector 430 is inserted within connector block 408. As a result, by positioning electrode 407 to be adjacent to connector 430 when lead body 402 is engaged within connector block 408, the present invention reduces the likelihood of direct muscle contact with electrode 410, reducing muscle stimulation around implantable medical device 400 during delivery of therapy by implantable medical device 400.

Figure 7:
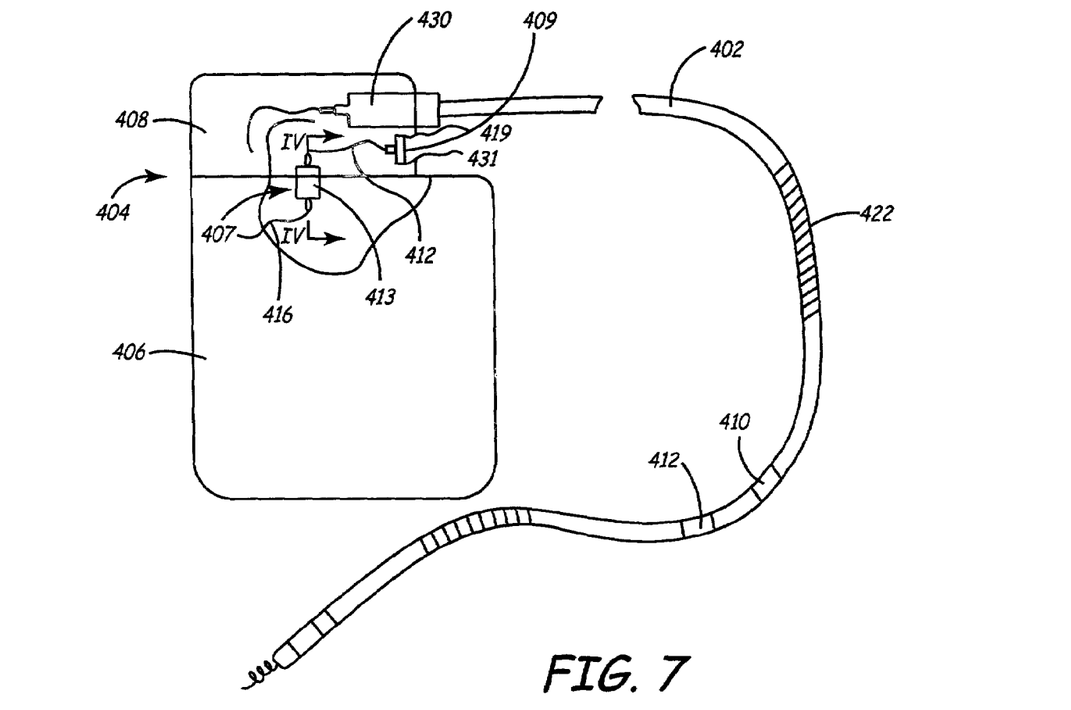
FIG. 7 is a schematic diagram of an implantable medical device for transmitting an electrical pulse according to an alternate embodiment of the present invention.

FIG. 7 is a schematic diagram of an implantable medical device for transmitting an electrical pulse according to an alternate embodiment of the present invention. As illustrated in FIG. 7, according to an alternate embodiment of the present invention, electrode 407 is positioned along housing 406 so that conductive element 409 is in close proximity to connector 430 of lead body 402. In particular, according to an alternate embodiment of the present invention, electrode 407 is positioned, similar to the embodiment of FIG. 6, along front portion 419 of connector block 408 so that when connector 430 of lead body 402 is engaged within connector block 408, direct muscle contact with conductive element 409 of electrode 407 is less likely to occur. In addition, in the alternate embodiment illustrated in FIG. 7, conductive element 409 of electrode 407 is embedded within control unit 404 of implantable medical device 400. In particular, for example, as illustrated in FIG. 7, conductive element 409 is positioned within an opening 431 located along front portion 419 of connector block 408 so that conductive element 409 is positioned in close proximity adjacent to connector 430 and below front portion 419 of connector block 408. In this way, by embedding conductive element 409 within connector block 408 of implantable medical device 400, the present invention further reduces the likelihood of direct muscle contact with electrode 407, reducing muscle stimulation around implantable medical device 400 during delivery of therapy by implantable medical device 400.

Figure 8:
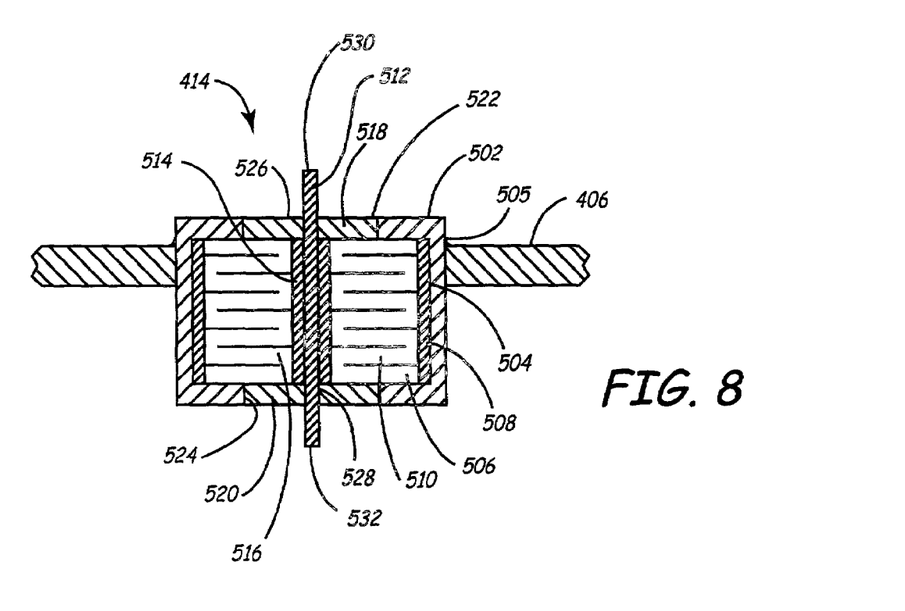
FIG. 8 is a cross-sectional view of an electrode according to the present invention, taken along cross-sectional line IV—IV of the implantable medical device of FIG. 6.

FIG. 8 is a cross-sectional view of an electrode according to the present invention, taken along cross-sectional line IV—IV of the implantable medical device of FIG. 6. As illustrated in FIG. 8, feedthrough 413 includes a hermetically sealed capsule 502 that, in the illustrated embodiment, extends through an opening 504 defined by housing 406. In the illustrated embodiment, capsule 502 is attached to housing 406 a weld 505, sealing any space left between capsule 502 and opening 504 in housing 406. A capacitor 506 is disposed within capsule 502 and is adhesively attached within capsule 502 by an electrically conductive adhesive 508 such that a first set of plates 510 are electrically coupled with capsule 502. A pin 512 extends through capacitor 506 and is adhesively attached to capacitor 506 by an electrically conductive adhesive 514 such that a second set of plates 516 of capacitor 506 are electrically coupled with pin 512. Electrically conductive adhesive 508 and electrically conductive adhesive 514 may be made from the same or different adhesive materials.

Still referring to FIG. 8, capsule 502 includes a first insulator 518 and a second insulator 520 disposed in and sealed to a first opening 522 and a second opening 524, respectively, defined by capsule 502. First insulator 518 and second insulator 520 define openings 526 and 528 therein, respectively, through which pin 512 extends. Thus, first insulator 522 and second insulator 520 provide electrical insulation between pin 512 and capsule 502. First conductor 412 electrically couples electrode 407 and a first end 530 of pin 512. Second conductor 416 electrically couples a second end 532 of pin 512 and one or more electrical components housed within the housing 406.

Figure 9:
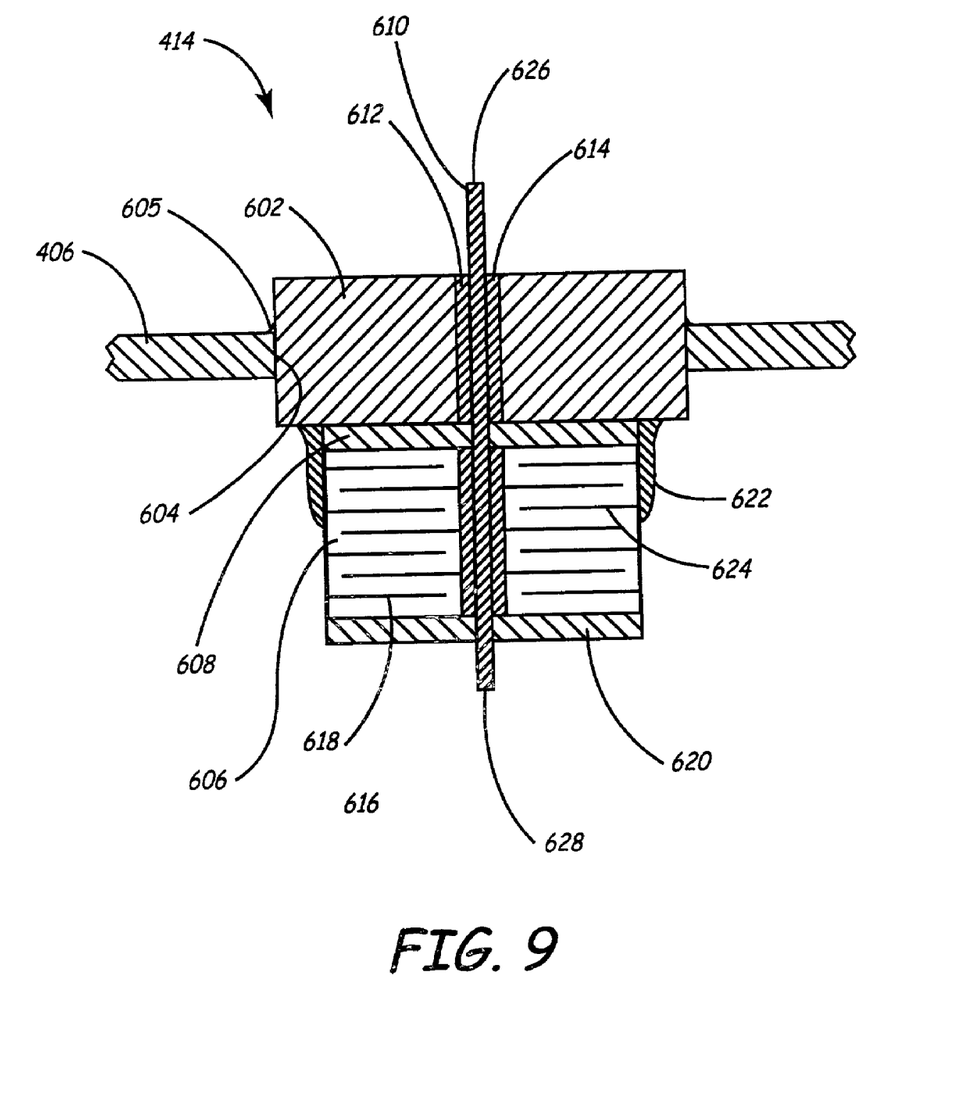
FIG. 9 is a cross-sectional view of an alternate embodiment of an electrode according to the present invention.

FIG. 9 is a cross-sectional view of an alternate embodiment of an electrode according to the present invention. As illustrated in FIG. 9, according to an alternate embodiment of the present invention, feedthrough 414 includes a ferrule 602 that, in the illustrated embodiment, extends through an opening 604 defined by housing 406. In the illustrated embodiment, ferrule 602 is attached to housing 406 by a weld 605, sealing any space left between ferrule 602 and opening 604 in housing 406. A capacitor 606 is spaced apart from ferrule 602 by a dielectric spacer 608. A pin 610 extends through capacitor 606 and through an insulator 612 disposed in an opening 614 defined by ferrule 602. Pin 610 is adhesively attached to capacitor 606 by an electrically conductive adhesive 616 such that a first set of plates 618 of capacitor 606 are electrically coupled with pin 610. A cap insulator 620 may also be attached to capacitor 606 such that pin 610 extends therethrough.

Capacitor 606 is adhesively attached to ferrule 602 by an electrically conductive adhesive 622 such that a second set of plates 624 of capacitor 606 is electrically coupled with ferrule 602. Electrically conductive adhesive 616 and electrically conductive adhesive 622 may be made from the same or different adhesive materials. Referring also to FIG. 6, first conductor 412 electrically couples electrode 410 with a first end 626 of pin 610. Further, second conductor 416 is attached to a second end 628 of pin 610 to couple feedthrough 414 and one or more electrical components housed within housing 406.

In certain cases, it may be desirable to transmit signals (e.g., pacing signals, stimulation signals, defibrillation signals, or the like) between lead electrode 410 and lead electrode 412, i.e., in a bipolar fashion. However, in order for a signal to be effectively transmitted between electrode 410 and 412 to appropriately stimulate the patient's heart, it is important that electrodes 410 and 412 be in sufficient electrical contact with tissue surrounding the area where electrodes 410 and 412 are placed within the patient. According to the present invention, once a signal has been transmitted between electrodes 410 and 412, microprocessor 224 determines whether electrodes 410 and 412 are in sufficient contact with the tissue of the patient to appropriately stimulate the heart. For example, microprocessor 224 determines whether the signal is effectively transmitted between electrodes 410 and 412 by examining the amplitude of subsequent p-waves sensed at electrodes 410 and 412 and determining that electrodes 410 and 412 are not in sufficient contact when the amplitude is less than a predetermined value. According to a preferred embodiment of the present invention, the predetermined value corresponds to a minimum amplitude threshold, for example, that is approximately equal to 1 mV, although it is understood that any minimum threshold could be utilized.

Microprocessor 224 then switches transmission of the signal, through switch matrix 208, so that the signal is transmitted between electrode 407 and one or both of electrodes 410 and 412 based upon review of the corresponding evoked response. In this way, the present invention provides an alternate path for the signals, such that the signals being transmitted from the one or both of lead electrode 410 and lead electrode 412 that is in sufficient electrical contact with the tissue of the body is transmitted through the body to electrode 407. As a result, a desired signal may be transmitted to the tissue of the body even though signals cannot be effectively transmitted between the lead electrode 410 and lead electrode 412. In addition, as described above, by positioning electrode 410 within close proximity to connector 430, muscle stimulation during delivery of therapy by implantable medical device 400 is reduced.

While the implantable medical device 100, 400 according to the present invention has been described above as including a bipolar lead, it is understood that the present invention is not intended to be applicable only in bipolar lead devices. Rather, implantable medical device 100, 400 of the present invention could also be utilized as a unipolar device, wherein electrical signals are transmitted between a single lead electrode (e.g., lead electrode 110, 410, lead electrode 112, 412, tip electrode 126, 426, or the like) and respective electrode 107, 407.

Figure 10:
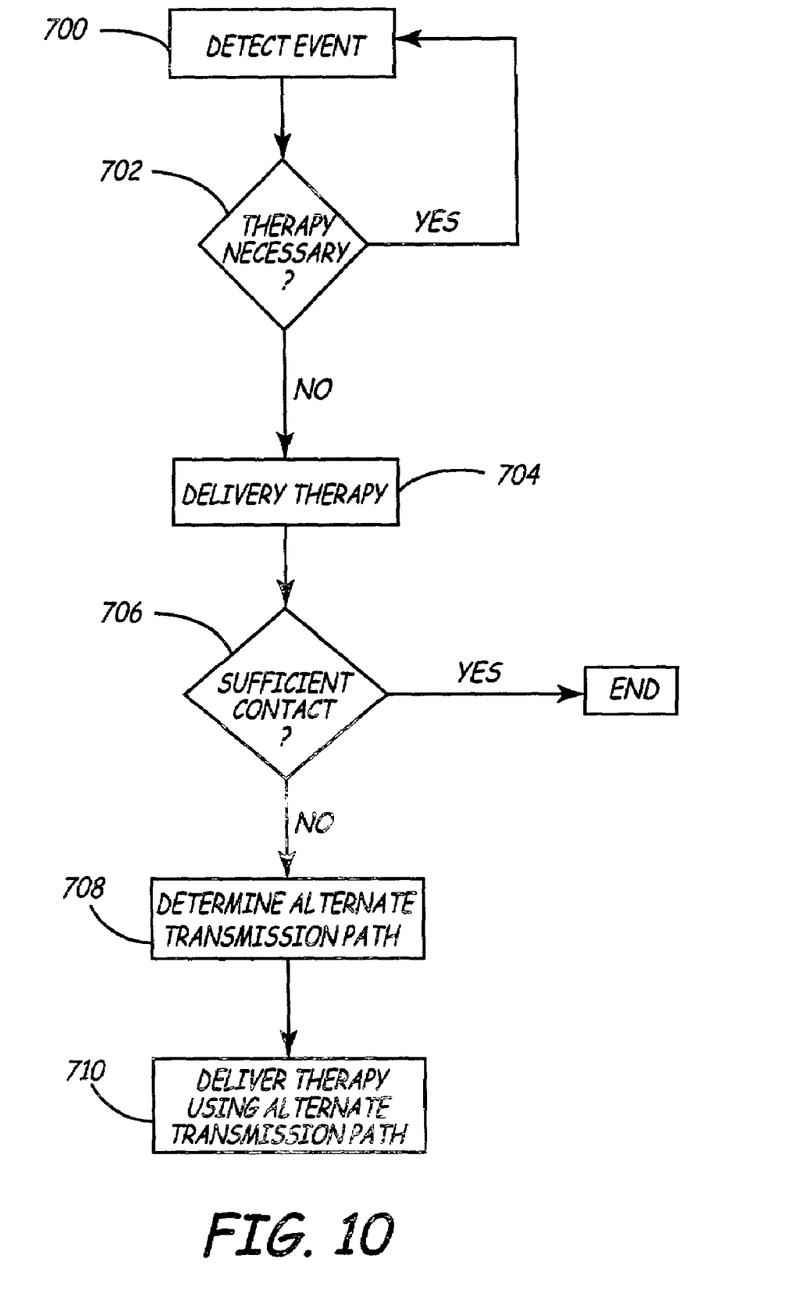
FIG. 10 is a flowchart of a method for transmitting an electrical pulse in an implantable medical device according to the present invention.

FIG. 10 is a flowchart of a method for transmitting an electrical pulse in an implantable medical device according to the present invention. As illustrated in FIG. 10, microprocessor 224 characterizes digitized signals corresponding to detected cardiac activity of the patient that are received by implantable medical device 100, 400, as described above, to recognize and classify the patient's heart rhythm employing any of the numerous signal processing methodologies known in the art, Step 700. Based on the classified detected heart rhythms, a determination is then made as to whether therapy is necessary, Step 702. If therapy is not necessary, the process is repeated for the next detected cardiac activity.

However, if therapy is necessary, microprocessor 224 transmits the corresponding signal between electrodes 110 and 112, Step 704.

Once the signal has been transmitted between electrodes 110 and 112, a determination is made as to whether the intended therapy is successful. For example, microprocessor 224 determines whether electrodes 110 and 112 are in sufficient contact to appropriately deliver the intended therapy, Step 706, as described above. If electrodes 110 and 112 are determined to be in sufficient contact, the process is repeated for the next detected cardiac activity, step 700. On the other hand, if one or both electrodes 110 and 112 are determined to not be in sufficient contact, an alternate transmission path is determined based on the determination of insufficient contact or on which of electrodes 110 and 112 are not in sufficient contact, Step 708. Once the alternate transmission path is determined, microprocessor 224 transmits a signal corresponding to the desired therapy using the alternate transmission path, Step 710.

In particular, according to a preferred embodiment of the present invention, once a signal corresponding to the appropriate therapy is transmitted, Step 704, microprocessor 224 determines whether electrodes 110 and 112 are in sufficient contact to appropriately stimulated heart 116 based on the amplitude of subsequent p-waves, for example, Step 706. If electrodes 110 and 112 are not in sufficient contact, microprocessor 224 transmits a signal corresponding to the desired therapy from electrode 107 to both electrode 110 and 112 in either a monophasic or a biphasic mode, Steps 708–710.

According to an alternate embodiment of the present invention, microprocessor 224 determines the alternate transmission path, Step 708, based upon whether one or both of electrodes 110 and 112 are in sufficient contact to appropriately stimulated heart 116, transmitting the subsequent signal from electrode 107 to the one electrode determined to be in sufficient contact, or to both electrodes such as when electrodes 110 and 112 may be in sufficient contact but improperly placed to appropriately stimulate. For example, if electrode 110 is determined to be in sufficient contact while electrode 112 is not, the alternate transmission path would be from electrode 107 to electrode 110, and if electrode 112 is determined to be in sufficient contact while electrode 110 is not, the alternate transmission path would be from electrode 107 to electrode 112. On the other hand, if it is determined that heart 116 is not sufficiently stimulated and that both or neither electrode 110 and electrode 112 are in sufficient contact, the alternate transmission path would be from electrode 107 to both electrode 110 and electrode 112, or from electrode 107 to any one of electrode 110 and electrode 112. Alternately, in response to heart 116 not being sufficiently stimulated, the alternate transmission path could also be from electrode 107 to both electrode 110 and electrode 112 or to any one of electrode 110 and electrode 112, irrespective of whether or not electrode 110 or electrode 112 is in sufficient contact.

Similarly, according to the present invention, when implantable medical device 400 is utilized, if therapy is determined to be necessary in Step 702, microprocessor 224 transmits the corresponding signal between electrodes 410 and 412, Step 704.

Once the signal has been transmitted between electrodes 410 and 412, a determination is made as to whether electrodes 410 and 412 are in sufficient contact to appropriately deliver the intended therapy, Step 706, as described above. If electrodes 410 and 412 are determined to be in sufficient contact, the process is repeated for the next detected cardiac activity, step 700. On the other hand, if one or both electrodes 410 and 412 are determined to not be in sufficient contact, an alternate transmission path is determined based on the determination of insufficient contact or on which of electrodes 410 and 412 are not in sufficient contact, Step 708. Once the alternate transmission path is determined, microprocessor 224 transmits a signal corresponding to the desired therapy using the alternate transmission path, Step 710.

In particular, according to a preferred embodiment of the present invention, once a signal corresponding to the appropriate therapy is transmitted, Step 704, microprocessor 224 determines whether electrodes 410 and 412 are in sufficient contact to appropriately stimulated heart 116 by examining the amplitude of subsequent p-waves, for example, Step 706. If electrodes 410 and 412 are not in sufficient contact, microprocessor 224 transmits a signal corresponding to the desired therapy from electrode 407 to both electrode 410 and 412 in either monophasic or biphasic mode, Steps 708–710.

According to an alternate embodiment of the present invention, microprocessor 224 determines the alternate transmission path, Step 708, based upon whether one or both of electrodes 410 and 412 are in sufficient contact to appropriately stimulated heart 116, transmitting the subsequent signal from electrode 407 to the one electrode determined to be in sufficient contact, or to both electrodes, such as when electrodes 410 and 412 may be in sufficient contact but improperly placed to appropriately stimulate heart 116. For example, if electrode 410 is determined to be in sufficient contact while electrode 412 is not, the alternate transmission path would be from electrode 407 to electrode 410, and if electrode 412 is determined to be in sufficient contact while electrode 410 is not, the alternate transmission path would be from electrode 407 to electrode 412. On the other hand, if it is determined that heart 116 is not sufficiently stimulated and that both or neither electrode 410 and electrode 412 are in sufficient contact, the alternate transmission path would be from electrode 407 to both electrode 410 and electrode 412, or from electrode 407 to any one of electrode 410 and electrode 412. Alternately, in response to heart 116 not being sufficiently stimulated, the alternate transmission path could also be from electrode 407 to both electrode 410 and electrode 412 or to any one of electrode 410 and electrode 412, irrespective of whether or not electrode 410 or electrode 412 is in sufficient contact.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

We claim:

1. An implantable medical device, comprising:
   an elongated lead body extending from a proximal portion to a distal portion;
   a first electrode and a second electrode positioned along the lead body;
   a housing having an upper portion;
   a control unit having a housing portion housing electrical components of the implantable medical device and a connector block positioned along an upper portion of the housing, the control unit transmitting a signal between the first electrode and the second electrode;

a connector positioned at the proximal portion of the lead body and insertable within the connector block to electrically couple the first electrode and the second electrode and the electrical components; and a third electrode having a conductive element positioned along the control unit in close proximity adjacent to the connector, wherein the control unit determines an alternate transmission path of the signal between the third electrode and one or both of the first electrode and the second electrode in response to the signal not being effectively transmitted between the first electrode and the second electrode as evidence by a sub-threshold amplitude of said signal compared to a predetermined minimum signal threshold value.

2. The implantable medical device of claim 1, wherein the third electrode is positioned along the housing.

3. The implantable medical device of claim 1, wherein the third electrode is positioned along the connector block.

4. The implantable medical device of claim 1, wherein the connector block extends from a back portion to a front portion and the upper portion of the housing extends outward from the front portion of the connector block, and wherein the third electrode is positioned along the outward extending upper portion of the housing.

5. The implantable medical device of claim 4, further comprising an opening formed along the outward extending upper portion, wherein the conductive element is positioned within the opening.

6. The implantable medical device of claim 2, wherein the conductive element is embedded within the housing.

7. The implantable medical device of claim 3, wherein the conductive element is embedded within the connector block.

8. The implantable medical device of claim 1, wherein the connector block extends from a back portion to a front portion and the third electrode is positioned along the front portion of the connector block.

9. The implantable medical device of claim 8, further comprising an opening formed along the front portion, wherein the conductor element is positioned within the opening.

10. The implantable medical device of claim 1, further comprising:

a microprocessor determining whether a signal is effectively transmitted between the first electrode and the second electrode; and a switch matrix switching transmission of the signal to an alternate transmission path between the third electrode and one or both of the first electrode and the second electrode in response to the signal not being effectively transmitted.

11. The implantable medical device of claim 10, wherein the alternate transmission path is in one of a monophasic and a biphasic mode.

12. An implantable medical device according to claim 1, wherein the signal comprises one of a high-energy cardiac defibrillation signal and a low-voltage cardiac pacing signal.

13. A method of transmitting a signal in an implantable medical device to deliver an intended therapy for stimulating a patient's heart, comprising the steps of:

transmitting the signal between a first electrode and a second electrode;

determining whether the intended therapy is successful;

in the event that that the intended therapy was not successful, then determining an alternate transmission path between a third electrode positioned in close proximity adjacent to a connector of the implantable medical device and one or both of the first electrode and the second electrode; and transmitting the signal along the alternate transmission path.

14. The method of claim 13, wherein the signal is transmitted along the alternate transmission path in one of a monophasic mode and a biphasic mode.

15. The method of claim 13, wherein the step of determining the alternate transmission path comprises determining which of the first electrode and the second electrode are in sufficient contact with the patient's heart.

16. The method of claim 15, wherein the alternate transmission path is between the third electrode and the first electrode in response to the first electrode being in sufficient contact.

17. The method of claim 15, wherein the alternate transmission path is between the third electrode and the second electrode in response to the second electrode being in sufficient contact.

18. The method of claim 15, wherein the alternate transmission path is between the third electrode and both the first electrode and the second electrode in response to one of the first electrode being in sufficient contact and and the second electrode not being in sufficient contact, the second electrode being in sufficient contact and the first electrode not being in sufficient contact, and both the first electrode and the second electrode not being in sufficient contact.

19. The method of claim 13, wherein in response to determining the therapy is not successful, the alternate transmission path is determined to be between the third electrode and one of the first electrode, the second electrode and both the first electrode and the second electrode.

20. A method according to claim 13, wherein the therapy comprises one of a high-energy defibrillation therapy and a low-energy cardiac pacing therapy.

* * * * *